US010701976B2

(12) United States Patent
Verleur et al.

(10) Patent No.: US 10,701,976 B2
(45) Date of Patent: Jul. 7, 2020

(54) VAPORIZER CARTRIDGE

(71) Applicant: VMR Products LLC, Miami, FL (US)

(72) Inventors: Jan Andries Verleur, Miami Beach, FL (US); Dan Recio, Miami Beach, FL (US); Zhiyuan Liu, Miami, FL (US); Hans Verleur, El Dorado, CA (US)

(73) Assignee: VMR Products, LLC, San Francisco, CA (US)

( * ) Notice: Subject to any disclaimer, the term of this patent is extended or adjusted under 35 U.S.C. 154(b) by 135 days.

(21) Appl. No.: 15/839,060

(22) Filed: Dec. 12, 2017

(65) Prior Publication Data
US 2018/0160737 A1    Jun. 14, 2018

Related U.S. Application Data

(60) Provisional application No. 62/433,012, filed on Dec. 12, 2016, provisional application No. 62/511,047, filed on May 25, 2017.

(51) Int. Cl.
*A61M 15/06* (2006.01)
*A24F 47/00* (2006.01)

(52) U.S. Cl.
CPC .......... *A24F 47/008* (2013.01); *A61M 15/06* (2013.01); *A61M 2209/045* (2013.01)

(58) Field of Classification Search
None
See application file for complete search history.

(56) References Cited

U.S. PATENT DOCUMENTS

| | | | |
|---|---|---|---|
| 4,303,083 A | 12/1981 | Burruss | |
| 4,651,770 A * | 3/1987 | Denham | F16K 3/08 137/270 |
| 4,938,236 A | 7/1990 | Banerjee et al. | |
| 4,945,448 A | 7/1990 | Bremenour et al. | |
| 5,175,791 A | 12/1992 | Muderlak et al. | |
| 5,842,601 A * | 12/1998 | Pierpoint | F41H 9/10 222/1 |
| 6,637,430 B1 * | 10/2003 | Voges | A61M 15/0065 128/200.14 |

(Continued)

FOREIGN PATENT DOCUMENTS

| | | | |
|---|---|---|---|
| AU | 2017202891 A1 | 5/2019 | |
| CA | 2641869 A1 | 5/2010 | |

(Continued)

OTHER PUBLICATIONS

International Search Report for PCT Application No. 2017/065764 dated Mar. 9, 2018 (5 pages).

*Primary Examiner* — Thor S Campbell
(74) *Attorney, Agent, or Firm* — Mintz Levin Cohn Ferris Glovsky and Popeo, P.C.

(57) ABSTRACT

A refillable cartridge for a vaporizer is disclosed. The refillable cartridge includes a body housing a reservoir for storing a vaporizing product. The refillable cartridge further includes a lower ceramic pad with a through hole providing access to the reservoir. The refillable cartridge further includes a lid slidably fastened to the upper end of the body. The refillable cartridge further includes an upper ceramic pad positioned at a lower end of the lid. The upper ceramic pad seals the through hole when the lid is slid to a first position and uncovers the through hole when the lid is slid to a second position.

14 Claims, 7 Drawing Sheets

(56) References Cited

U.S. PATENT DOCUMENTS

| | | | |
|---|---|---|---|
| 6,708,846 | B1 | 3/2004 | Fuchs et al. |
| 6,929,154 | B2* | 8/2005 | Grey .................. A61M 15/009 |
| | | | 222/153.03 |
| 7,832,410 | B2 | 11/2010 | Hon |
| 7,913,686 | B2 | 3/2011 | Hughes et al. |
| 8,205,622 | B2 | 6/2012 | Pan |
| 8,678,012 | B2 | 3/2014 | Li et al. |
| 8,689,789 | B2 | 4/2014 | Andrus et al. |
| 8,739,786 | B2* | 6/2014 | Postma ................ A61M 11/041 |
| | | | 128/203.26 |
| 8,899,240 | B2 | 12/2014 | Mass |
| 8,991,402 | B2 | 3/2015 | Bowen et al. |
| 9,038,642 | B2 | 5/2015 | Liu |
| 9,055,617 | B2 | 6/2015 | Thorens et al. |
| 9,055,770 | B2 | 6/2015 | Liu |
| 9,072,322 | B2 | 7/2015 | Liu |
| 9,078,474 | B2 | 7/2015 | Thompson |
| 9,078,475 | B2 | 7/2015 | Li et al. |
| 9,089,168 | B2 | 7/2015 | Liu |
| 9,101,729 | B2 | 8/2015 | Liu |
| 9,113,659 | B2 | 8/2015 | Liu |
| 9,155,336 | B2 | 10/2015 | Liu |
| 9,167,849 | B2 | 10/2015 | Adamic |
| 9,198,466 | B2 | 12/2015 | Liu |
| 9,220,303 | B2 | 12/2015 | Li et al. |
| 9,226,526 | B2 | 1/2016 | Liu |
| 9,247,773 | B2 | 2/2016 | Memari et al. |
| 9,254,007 | B2 | 2/2016 | Liu |
| 9,332,787 | B2 | 5/2016 | Liu |
| 9,351,522 | B2 | 5/2016 | Safari |
| 9,360,379 | B2 | 6/2016 | Liu |
| 9,364,025 | B2 | 6/2016 | Liu |
| 9,414,627 | B2 | 8/2016 | Liu |
| 9,414,628 | B2 | 8/2016 | Liu |
| 9,420,831 | B2 | 8/2016 | Liu |
| 9,427,023 | B2 | 8/2016 | Liu |
| 9,439,455 | B2 | 9/2016 | Alarcon et al. |
| 9,439,456 | B2 | 9/2016 | Liu |
| 9,456,633 | B2 | 10/2016 | Liu |
| 9,497,994 | B2 | 11/2016 | Liu |
| 9,497,997 | B2 | 11/2016 | Wu |
| 9,497,998 | B2 | 11/2016 | Chen |
| 9,498,001 | B2 | 11/2016 | Wu |
| 9,504,279 | B2 | 11/2016 | Chen |
| 9,510,624 | B2 | 12/2016 | Li et al. |
| 9,538,787 | B2 | 1/2017 | Liu |
| 9,554,596 | B2 | 1/2017 | Liu |
| 9,572,374 | B2 | 2/2017 | Gabbay |
| 9,603,198 | B2 | 3/2017 | Liu |
| 9,622,511 | B2 | 4/2017 | Zhu |
| 9,668,522 | B2* | 6/2017 | Memari ................ A24F 15/12 |
| 9,675,113 | B2 | 6/2017 | Liu |
| 9,675,118 | B2 | 6/2017 | Chen |
| 9,681,687 | B2 | 6/2017 | Liu |
| 9,693,586 | B2 | 7/2017 | Liu |
| 9,693,588 | B2 | 7/2017 | Zhu |
| 9,700,075 | B2 | 7/2017 | Liu |
| 9,723,872 | B2 | 8/2017 | Liu |
| 9,730,471 | B2 | 8/2017 | Li et al. |
| 9,772,216 | B2 | 9/2017 | Poole et al. |
| 9,814,269 | B2 | 11/2017 | Li et al. |
| 9,877,521 | B1* | 1/2018 | Gillis .................. A24F 47/008 |
| 9,999,250 | B2 | 6/2018 | Minskoff et al. |
| 10,383,368 | B2* | 8/2019 | Larson ................ A24F 47/008 |
| 10,412,996 | B2* | 9/2019 | Bright ................ A24F 47/008 |
| 2001/0032643 | A1 | 10/2001 | Hochrainer et al. |
| 2005/0266365 | A1 | 12/2005 | Xie |
| 2005/0279350 | A1* | 12/2005 | Rasor .................. A61H 33/14 |
| | | | 128/200.14 |
| 2006/0166466 | A1* | 7/2006 | Maki ................ H01L 21/67132 |
| | | | 438/464 |
| 2007/0062548 | A1 | 3/2007 | Horstmann et al. |
| 2008/0251547 | A1* | 10/2008 | Ruiz de Gopegui ........................ |
| | | | B05B 7/2435 |
| | | | 222/635 |
| 2009/0071469 | A1 | 3/2009 | Abrams |
| 2009/0192443 | A1 | 7/2009 | Collins |
| 2009/0260641 | A1 | 10/2009 | Monsees et al. |
| 2010/0242975 | A1* | 9/2010 | Hearn .................. A24F 47/002 |
| | | | 131/273 |
| 2011/0036363 | A1 | 2/2011 | Urtsev et al. |
| 2011/0226236 | A1 | 9/2011 | Buchberger |
| 2011/0297166 | A1 | 12/2011 | Takeuchi et al. |
| 2012/0167906 | A1* | 7/2012 | Gysland ................ A24F 47/008 |
| | | | 131/328 |
| 2012/0199663 | A1 | 8/2012 | Qiu |
| 2012/0248005 | A1 | 10/2012 | Bergey |
| 2012/0298676 | A1 | 11/2012 | Cooks |
| 2013/0078025 | A1* | 3/2013 | Turgeman ............ B41J 2/17513 |
| | | | 401/258 |
| 2013/0087160 | A1 | 4/2013 | Gherghe |
| 2013/0180533 | A1 | 7/2013 | Kim et al. |
| 2013/0199528 | A1 | 8/2013 | Goodman et al. |
| 2013/0213418 | A1 | 8/2013 | Tucker et al. |
| 2013/0263869 | A1 | 10/2013 | Zhu |
| 2013/0327327 | A1* | 12/2013 | Edwards ............ A61M 15/0028 |
| | | | 128/203.11 |
| 2014/0007891 | A1 | 1/2014 | Liu |
| 2014/0041658 | A1 | 2/2014 | Goodman et al. |
| 2014/0060528 | A1 | 3/2014 | Liu |
| 2014/0060556 | A1 | 3/2014 | Liu |
| 2014/0076310 | A1* | 3/2014 | Newton ................ A61M 15/06 |
| | | | 128/202.21 |
| 2014/0109921 | A1 | 4/2014 | Chen |
| 2014/0130817 | A1 | 5/2014 | Li et al. |
| 2014/0150783 | A1 | 6/2014 | Liu |
| 2014/0150785 | A1 | 6/2014 | Malik et al. |
| 2014/0209108 | A1 | 7/2014 | Li et al. |
| 2014/0216484 | A1 | 8/2014 | Liu |
| 2014/0230835 | A1 | 8/2014 | Saliman |
| 2014/0246031 | A1 | 9/2014 | Liu |
| 2014/0261487 | A1 | 9/2014 | Chapman et al. |
| 2014/0290673 | A1 | 10/2014 | Liu |
| 2014/0305451 | A1 | 10/2014 | Liu |
| 2014/0311503 | A1 | 10/2014 | Liu |
| 2014/0311505 | A1 | 10/2014 | Liu |
| 2014/0332017 | A1 | 11/2014 | Liu |
| 2014/0338684 | A1 | 11/2014 | Liu |
| 2014/0360516 | A1 | 12/2014 | Liu |
| 2014/0373833 | A1 | 12/2014 | Liu |
| 2014/0376895 | A1 | 12/2014 | Han |
| 2015/0007836 | A1 | 1/2015 | Li et al. |
| 2015/0047658 | A1 | 2/2015 | Cyphert et al. |
| 2015/0047663 | A1 | 2/2015 | Liu |
| 2015/0053215 | A1 | 2/2015 | Liu |
| 2015/0059787 | A1 | 3/2015 | Qiu |
| 2015/0101623 | A1 | 4/2015 | Liu |
| 2015/0101945 | A1 | 4/2015 | Scatterday |
| 2015/0114410 | A1 | 4/2015 | Doster |
| 2015/0114504 | A1 | 4/2015 | Cecka et al. |
| 2015/0128970 | A1 | 5/2015 | Liu |
| 2015/0128973 | A1 | 5/2015 | Li et al. |
| 2015/0128977 | A1 | 5/2015 | Li et al. |
| 2015/0144145 | A1 | 5/2015 | Chang et al. |
| 2015/0144147 | A1 | 5/2015 | Li et al. |
| 2015/0150307 | A1 | 6/2015 | Liu |
| 2015/0157053 | A1 | 6/2015 | Mayor |
| 2015/0157054 | A1 | 6/2015 | Liu |
| 2015/0164146 | A1 | 6/2015 | Li et al. |
| 2015/0173422 | A1 | 6/2015 | Liu |
| 2015/0181928 | A1 | 7/2015 | Liu |
| 2015/0181937 | A1 | 7/2015 | Dubief et al. |
| 2015/0181940 | A1 | 7/2015 | Liu |
| 2015/0181941 | A1 | 7/2015 | Liu |
| 2015/0181944 | A1 | 7/2015 | Li et al. |
| 2015/0189915 | A1 | 7/2015 | Liu |
| 2015/0189918 | A1 | 7/2015 | Liu |
| 2015/0189919 | A1 | 7/2015 | Liu |
| 2015/0196059 | A1 | 7/2015 | Liu |
| 2015/0201674 | A1 | 7/2015 | Dooly et al. |
| 2015/0216234 | A1 | 8/2015 | Chung |

(56) References Cited

U.S. PATENT DOCUMENTS

| | | |
|---|---|---|
| 2015/0223521 A1 | 8/2015 | Menting et al. |
| 2015/0223522 A1 | 8/2015 | Ampolini et al. |
| 2015/0245654 A1 | 9/2015 | Memari et al. |
| 2015/0245665 A1 | 9/2015 | Memari et al. |
| 2015/0257447 A1 | 9/2015 | Sullivan |
| 2015/0272217 A1 | 10/2015 | Chen |
| 2015/0272218 A1 | 10/2015 | Chen |
| 2015/0282530 A1 | 10/2015 | Johnson et al. |
| 2015/0289565 A1 | 10/2015 | Cadieux et al. |
| 2015/0296887 A1 | 10/2015 | Zhu |
| 2015/0305403 A1 | 10/2015 | Coelho |
| 2015/0305406 A1 | 10/2015 | Li et al. |
| 2015/0313287 A1 | 11/2015 | Verleur et al. |
| 2015/0313288 A1 | 11/2015 | Liu |
| 2015/0336689 A1 | 11/2015 | Brown et al. |
| 2015/0342255 A1 | 12/2015 | Wu |
| 2015/0342256 A1 | 12/2015 | Chen |
| 2015/0342257 A1 | 12/2015 | Chen |
| 2015/0342258 A1* | 12/2015 | Chen .................. H05B 3/06 131/329 |
| 2015/0351454 A1 | 12/2015 | Huang |
| 2015/0351457 A1 | 12/2015 | Liu |
| 2015/0359265 A1 | 12/2015 | Liu |
| 2015/0366267 A1 | 12/2015 | Liu |
| 2016/0000147 A1 | 1/2016 | Li et al. |
| 2016/0007653 A1 | 1/2016 | Tu |
| 2016/0015082 A1 | 1/2016 | Liu |
| 2016/0018347 A1 | 1/2016 | Drbal et al. |
| 2016/0029699 A1 | 2/2016 | Li et al. |
| 2016/0044964 A1 | 2/2016 | Liu |
| 2016/0044965 A1 | 2/2016 | Liu |
| 2016/0058073 A1 | 3/2016 | Chen |
| 2016/0058074 A1 | 3/2016 | Liu |
| 2016/0073694 A1 | 3/2016 | Liu |
| 2016/0091194 A1 | 3/2016 | Liu |
| 2016/0120218 A1 | 5/2016 | Schennum et al. |
| 2016/0120226 A1 | 5/2016 | Rado |
| 2016/0128384 A1 | 5/2016 | Luciani |
| 2016/0128387 A1 | 5/2016 | Chen |
| 2016/0129205 A1 | 5/2016 | Shahaf et al. |
| 2016/0135506 A1 | 5/2016 | Sanchez et al. |
| 2016/0143360 A1 | 5/2016 | Sanchez et al. |
| 2016/0150824 A1 | 6/2016 | Memari et al. |
| 2016/0167846 A1 | 6/2016 | Zahr et al. |
| 2016/0183597 A1 | 6/2016 | Li et al. |
| 2016/0192705 A1 | 7/2016 | Borkovec et al. |
| 2016/0192707 A1 | 7/2016 | Li et al. |
| 2016/0192708 A1 | 7/2016 | Demeritt et al. |
| 2016/0192710 A1 | 7/2016 | Liu |
| 2016/0198767 A1 | 7/2016 | Verleur |
| 2016/0198769 A1 | 7/2016 | Liu |
| 2016/0198770 A1 | 7/2016 | Alarcon |
| 2016/0200463 A1 | 7/2016 | Hodges et al. |
| 2016/0205999 A1 | 7/2016 | Liu |
| 2016/0213061 A1 | 7/2016 | Liu |
| 2016/0213866 A1 | 7/2016 | Tan |
| 2016/0219934 A1 | 8/2016 | Li et al. |
| 2016/0227838 A1 | 8/2016 | Johnson et al. |
| 2016/0235120 A1 | 8/2016 | Liu |
| 2016/0235124 A1 | 8/2016 | Krietzman |
| 2016/0249680 A1 | 9/2016 | Liu |
| 2016/0262454 A1 | 9/2016 | Sears et al. |
| 2016/0262455 A1 | 9/2016 | Chen |
| 2016/0270442 A1 | 9/2016 | Liu |
| 2016/0286860 A1 | 10/2016 | Flayler |
| 2016/0286865 A1 | 10/2016 | King et al. |
| 2016/0295913 A1 | 10/2016 | Guo et al. |
| 2016/0295925 A1 | 10/2016 | Chen |
| 2016/0302487 A1 | 10/2016 | Chen |
| 2016/0309789 A1 | 10/2016 | Thomas |
| 2016/0325858 A1 | 11/2016 | Ampolini et al. |
| 2016/0331028 A1 | 11/2016 | Xu |
| 2016/0332754 A1 | 11/2016 | Brown et al. |
| 2016/0338408 A1 | 11/2016 | Guenther et al. |
| 2016/0338410 A1 | 11/2016 | Batista et al. |
| 2016/0338411 A1 | 11/2016 | Liu |
| 2016/0345629 A1 | 12/2016 | Mironov |
| 2016/0345630 A1 | 12/2016 | Mironov et al. |
| 2016/0345636 A1 | 12/2016 | Liu |
| 2016/0360788 A1 | 12/2016 | Wang |
| 2016/0360789 A1 | 12/2016 | Hawes et al. |
| 2016/0360792 A1 | 12/2016 | Liu |
| 2016/0366942 A1 | 12/2016 | Liu |
| 2016/0366945 A1 | 12/2016 | Rado |
| 2017/0006915 A1 | 1/2017 | Li et al. |
| 2017/0006916 A1 | 1/2017 | Liu |
| 2017/0006919 A1 | 1/2017 | Liu |
| 2017/0006920 A1 | 1/2017 | Liu |
| 2017/0006922 A1 | 1/2017 | Wang et al. |
| 2017/0013875 A1 | 1/2017 | Schennum et al. |
| 2017/0013881 A1 | 1/2017 | Liu |
| 2017/0013885 A1 | 1/2017 | Qiu |
| 2017/0027221 A1 | 2/2017 | Liu |
| 2017/0027880 A1 | 2/2017 | Yamaguchi et al. |
| 2017/0035109 A1 | 2/2017 | Liu |
| 2017/0042225 A1 | 2/2017 | Liu |
| 2017/0042246 A1 | 2/2017 | Lau et al. |
| 2017/0049153 A1 | 2/2017 | Guo et al. |
| 2017/0049156 A1 | 2/2017 | Wang et al. |
| 2017/0055579 A1 | 3/2017 | Kuna et al. |
| 2017/0071256 A1 | 3/2017 | Verleur et al. |
| 2017/0071260 A1 | 3/2017 | Li et al. |
| 2017/0079322 A1 | 3/2017 | Li et al. |
| 2017/0079324 A1 | 3/2017 | Eksouzian |
| 2017/0079328 A1 | 3/2017 | Wu |
| 2017/0079332 A1 | 3/2017 | Li et al. |
| 2017/0095000 A1 | 4/2017 | Spirito et al. |
| 2017/0105453 A1 | 4/2017 | Li et al. |
| 2017/0112192 A1 | 4/2017 | Shan |
| 2017/0119060 A1 | 5/2017 | Li et al. |
| 2017/0135398 A1 | 5/2017 | Scott et al. |
| 2017/0143040 A1 | 5/2017 | Liu |
| 2017/0156400 A1 | 6/2017 | Liu |
| 2017/0156401 A1 | 6/2017 | Liu |
| 2017/0156408 A1 | 6/2017 | Li et al. |
| 2017/0157341 A1 | 6/2017 | Pandya et al. |
| 2017/0170439 A1 | 6/2017 | Jarvis et al. |
| 2017/0172209 A1 | 6/2017 | Saydar et al. |
| 2017/0172210 A1* | 6/2017 | Bright .................. A24F 47/008 |
| 2017/0172212 A1* | 6/2017 | Phillips ................ A24F 47/008 |
| 2017/0181476 A1 | 6/2017 | Li et al. |
| 2017/0196267 A1 | 7/2017 | Zou et al. |
| 2017/0196272 A1 | 7/2017 | Li et al. |
| 2017/0197046 A1 | 7/2017 | Buchberger |
| 2017/0202268 A1 | 7/2017 | Li et al. |
| 2017/0208858 A1 | 7/2017 | Li |
| 2017/0208865 A1 | 7/2017 | Nettenstrom et al. |
| 2017/0208869 A1 | 7/2017 | Li et al. |
| 2017/0208870 A1 | 7/2017 | Liu |
| 2017/0214261 A1 | 7/2017 | Gratton |
| 2017/0215481 A1 | 8/2017 | Li et al. |
| 2017/0222468 A1 | 8/2017 | Schennum et al. |
| 2017/0224017 A1 | 8/2017 | Li et al. |
| 2017/0224018 A1 | 8/2017 | Li et al. |
| 2017/0231283 A1 | 8/2017 | Gadas |
| 2017/0233114 A1 | 8/2017 | Christensen et al. |
| 2017/0238617 A1 | 8/2017 | Scatterday |
| 2017/0251718 A1 | 9/2017 | Armoush et al. |
| 2017/0251729 A1 | 9/2017 | Li et al. |
| 2017/0273358 A1 | 9/2017 | Batista et al. |
| 2017/0273359 A1 | 9/2017 | Liu |
| 2017/0280771 A1 | 10/2017 | Courbat et al. |
| 2017/0280778 A1 | 10/2017 | Force |
| 2017/0281883 A1 | 10/2017 | Li et al. |
| 2017/0295846 A1 | 10/2017 | Liu |
| 2017/0295847 A1 | 10/2017 | Liu |
| 2017/0325289 A1 | 11/2017 | Liu |
| 2017/0325504 A1 | 11/2017 | Liu |
| 2017/0340009 A1 | 11/2017 | Hon |
| 2017/0340018 A1* | 11/2017 | Thorens ............... A24F 47/008 |
| 2017/0347706 A1 | 12/2017 | Aoun et al. |
| 2017/0347709 A1 | 12/2017 | Laakso et al. |
| 2017/0360098 A1 | 12/2017 | Newcomb et al. |
| 2018/0000156 A1 | 1/2018 | Qiu |

(56) References Cited

U.S. PATENT DOCUMENTS

| | | |
|---|---|---|
| 2018/0014577 A1 | 1/2018 | Qiu |
| 2018/0016040 A1 | 1/2018 | Ewing et al. |
| 2018/0027881 A1 | 2/2018 | Chen |
| 2018/0035718 A1 | 2/2018 | Liu |
| 2018/0042299 A1 | 2/2018 | Han et al. |
| 2018/0044162 A1 | 2/2018 | Scott et al. |
| 2018/0064172 A1 | 3/2018 | Qiu |
| 2018/0077967 A1 | 3/2018 | Hatton et al. |
| 2018/0084828 A1 | 3/2018 | Phillips et al. |
| 2018/0098575 A1 | 4/2018 | Liu |
| 2018/0110940 A1 | 4/2018 | Suzuki et al. |
| 2018/0134429 A1 | 5/2018 | Slurink |
| 2018/0140014 A1 | 5/2018 | Yu et al. |
| 2018/0153219 A1 | 6/2018 | Verleur et al. |
| 2018/0160735 A1 | 6/2018 | Borkovec et al. |
| 2018/0160737 A1 | 6/2018 | Verleur et al. |
| 2018/0160738 A1 | 6/2018 | Verleur et al. |
| 2018/0161525 A1 | 6/2018 | Liu et al. |
| 2018/0170588 A1 | 6/2018 | Boldrini |
| 2018/0279682 A1 | 10/2018 | Guo et al. |
| 2018/0303160 A1* | 10/2018 | Davis ............... A24F 47/008 |
| 2018/0364745 A1* | 12/2018 | Chamot ............ G05D 23/1353 |
| 2019/0037926 A1 | 2/2019 | Qiu |
| 2019/0069601 A1 | 3/2019 | Qiu |
| 2019/0166909 A1* | 6/2019 | Reevell ............... A24F 47/008 |
| 2019/0254349 A1* | 8/2019 | Davis ............... A24F 47/008 |

FOREIGN PATENT DOCUMENTS

| | | |
|---|---|---|
| CN | 201781984 U | 4/2011 |
| CN | 203040683 U | 7/2013 |
| CN | 203234036 U | 10/2013 |
| CN | 203314104 U | 12/2013 |
| CN | 102727969 B | 2/2014 |
| CN | 203467677 U | 3/2014 |
| CN | 203618789 U | 6/2014 |
| CN | 204132390 U | 2/2015 |
| CN | 104382237 A | 3/2015 |
| CN | 204180941 U | 3/2015 |
| CN | 204861164 U | 12/2015 |
| CN | 204907937 U | 12/2015 |
| CN | 105249536 A | 1/2016 |
| CN | 105249536 A | 1/2016 |
| CN | 205284996 U | 6/2016 |
| CN | 205284996 U | 6/2016 |
| CN | 205305995 U | 6/2016 |
| CN | 205305995 U | 6/2016 |
| CN | 103750571 B | 7/2016 |
| CN | 205358224 U | 7/2016 |
| CN | 205358227 U | 7/2016 |
| CN | 205358227 U | 7/2016 |
| CN | 205390306 U | 7/2016 |
| CN | 205409676 U | 8/2016 |
| CN | 205409676 U | 8/2016 |
| CN | 105962419 A | 9/2016 |
| CN | 106686996 A | 5/2017 |
| CN | 106686996 A | 5/2017 |
| CN | 206821974 U | 1/2018 |
| CN | 104939326 B | 4/2018 |
| CN | 105919164 B | 3/2019 |
| EP | 2875741 A2 | 5/2015 |
| EP | 2952110 | 12/2015 |
| EP | 3075270 A1 | 10/2016 |
| EP | 3097803 A1 | 11/2016 |
| EP | 3103356 A1 | 12/2016 |
| EP | 3135139 A1 | 3/2017 |
| EP | 3143884 A3 | 3/2017 |
| EP | 3165102 A3 | 5/2017 |
| EP | 3199043 A1 | 8/2017 |
| EP | 3047742 B1 | 3/2018 |
| EP | 3130238 A1 | 5/2018 |
| EP | 3143882 A3 | 11/2018 |
| EP | 3155908 A1 | 12/2018 |
| TW | 201524383 | 7/2015 |
| WO | WO2012059726 A2 | 5/2012 |
| WO | WO2012129812 A1 | 10/2012 |
| WO | WO2012173322 A1 | 12/2012 |
| WO | WO2012174677 A1 | 12/2012 |
| WO | WO2013020220 A1 | 2/2013 |
| WO | WO2013044537 | 4/2013 |
| WO | WO2013110208 A1 | 8/2013 |
| WO | WO2013110210 A1 | 8/2013 |
| WO | WO2013113173 A1 | 8/2013 |
| WO | WO2013113174 A1 | 8/2013 |
| WO | WO2013116983 A1 | 8/2013 |
| WO | WO2013174001 A1 | 11/2013 |
| WO | WO2014047948 A1 | 4/2014 |
| WO | WO2014071747 A1 | 5/2014 |
| WO | WO2014144678 A2 | 9/2014 |
| WO | WO2014147470 A2 | 9/2014 |
| WO | WO2014161181 A1 | 10/2014 |
| WO | WO2014169667 A1 | 10/2014 |
| WO | WO2014201664 A1 | 12/2014 |
| WO | WO2015010291 A1 | 1/2015 |
| WO | WO2015021646 A1 | 2/2015 |
| WO | WO2015021651 A1 | 2/2015 |
| WO | WO2015027436 A1 | 3/2015 |
| WO | WO2015032055 A1 | 3/2015 |
| WO | WO2015032093 A1 | 3/2015 |
| WO | WO2015039280 A1 | 3/2015 |
| WO | WO2015039332 A1 | 3/2015 |
| WO | WO2015058387 A1 | 4/2015 |
| WO | WO2015070398 A1 | 5/2015 |
| WO | WO2015070405 A1 | 5/2015 |
| WO | WO2015074187 A1 | 5/2015 |
| WO | WO2015077999 A1 | 6/2015 |
| WO | WO2015078010 A1 | 6/2015 |
| WO | WO2015079197 A1 | 6/2015 |
| WO | WO2015106434 A1 | 7/2015 |
| WO | WO2015120591 A1 | 8/2015 |
| WO | WO2015120623 A1 | 8/2015 |
| WO | WO2015143765 A1 | 10/2015 |
| WO | WO2015154309 A1 | 10/2015 |
| WO | WO2015157891 A1 | 10/2015 |
| WO | WO2015157893 A1 | 10/2015 |
| WO | WO2015157900 A1 | 10/2015 |
| WO | WO2015165067 A1 | 11/2015 |
| WO | WO2015165081 A1 | 11/2015 |
| WO | WO2015165105 A1 | 11/2015 |
| WO | WO2015168912 A1 | 11/2015 |
| WO | WO2015172606 A1 | 11/2015 |
| WO | WO2015174657 A1 | 11/2015 |
| WO | WO2015176300 A1 | 11/2015 |
| WO | WO2015176580 A1 | 11/2015 |
| WO | WO2015180027 A1 | 12/2015 |
| WO | WO2015180088 A1 | 12/2015 |
| WO | WO2015184590 A1 | 12/2015 |
| WO | WO2015190810 A1 | 12/2015 |
| WO | WO2016000113 A1 | 1/2016 |
| WO | WO2016000130 A1 | 1/2016 |
| WO | WO2016000136 A1 | 1/2016 |
| WO | WO2016000139 A1 | 1/2016 |
| WO | WO2016000206 A1 | 1/2016 |
| WO | WO2016000214 A1 | 1/2016 |
| WO | WO2016000232 A1 | 1/2016 |
| WO | WO2016023181 A1 | 2/2016 |
| WO | WO2016023182 A1 | 2/2016 |
| WO | WO2016023183 A1 | 2/2016 |
| WO | WO2016023212 A1 | 2/2016 |
| WO | WO2016026104 A1 | 2/2016 |
| WO | WO2016026156 A1 | 2/2016 |
| WO | WO2016029386 A1 | 3/2016 |
| WO | WO2016029389 A1 | 3/2016 |
| WO | WO2016029468 A1 | 3/2016 |
| WO | WO2016029470 A1 | 3/2016 |
| WO | WO2016029473 A1 | 3/2016 |
| WO | WO2016029567 A1 | 3/2016 |
| WO | WO2016041209 A1 | 3/2016 |
| WO | WO2016049822 A1 | 4/2016 |
| WO | WO2016049823 A1 | 4/2016 |
| WO | WO2016049855 A1 | 4/2016 |
| WO | WO2016058139 A1 | 4/2016 |
| WO | WO2016061729 A1 | 4/2016 |
| WO | WO2016061730 A1 | 4/2016 |

(56) References Cited

FOREIGN PATENT DOCUMENTS

| | | |
|---|---|---|
| WO | WO2016061822 A1 | 4/2016 |
| WO | WO2016065532 A1 | 5/2016 |
| WO | WO2016065599 A1 | 5/2016 |
| WO | WO2016065606 A1 | 5/2016 |
| WO | WO2016070553 A1 | 5/2016 |
| WO | WO2016082103 A1 | 6/2016 |
| WO | WO2016082158 A1 | 6/2016 |
| WO | WO2016082179 A1 | 6/2016 |
| WO | WO2016082180 A1 | 6/2016 |
| WO | WO2016090531 A1 | 6/2016 |
| WO | WO2016090602 A1 | 6/2016 |
| WO | WO2016090955 A1 | 6/2016 |
| WO | WO2016095220 A1 | 6/2016 |
| WO | WO2016095234 A1 | 6/2016 |
| WO | WO2016101150 A1 | 6/2016 |
| WO | WO2016103202 A1 | 6/2016 |
| WO | WO2016106495 A1 | 7/2016 |
| WO | WO2016108694 A1 | 7/2016 |
| WO | WO2016109930 A1 | 7/2016 |
| WO | WO2016109931 A1 | 7/2016 |
| WO | WO2016109932 A1 | 7/2016 |
| WO | WO2016109964 A1 | 7/2016 |
| WO | WO2016112533 A1 | 7/2016 |
| WO | WO2016112534 A1 | 7/2016 |
| WO | WO2016115701 A1 | 7/2016 |
| WO | WO2016119101 A1 | 8/2016 |
| WO | WO2016119225 A1 | 8/2016 |
| WO | WO2016119496 A1 | 8/2016 |
| WO | WO2016122417 A1 | 8/2016 |
| WO | WO2016123763 A1 | 8/2016 |
| WO | WO2016123770 A1 | 8/2016 |
| WO | WO2016123781 A1 | 8/2016 |
| WO | WO2016127293 A1 | 8/2016 |
| WO | WO2016127360 A1 | 8/2016 |
| WO | WO2016127389 A1 | 8/2016 |
| WO | WO2016127390 A1 | 8/2016 |
| WO | WO2016127396 | 8/2016 |
| WO | WO2016127406 A1 | 8/2016 |
| WO | WO2016127468 A1 | 8/2016 |
| WO | WO2016127839 A1 | 8/2016 |
| WO | WO2016132026 A1 | 8/2016 |
| WO | WO2016134544 A1 | 9/2016 |
| WO | WO2016138608 A1 | 9/2016 |
| WO | WO2016138665 A1 | 9/2016 |
| WO | WO2016141508 A1 | 9/2016 |
| WO | WO2016141555 A1 | 9/2016 |
| WO | WO2016141556 A1 | 9/2016 |
| WO | WO2016141592 A1 | 9/2016 |
| WO | WO2016141593 A1 | 9/2016 |
| WO | WO2016145611 A1 | 9/2016 |
| WO | WO2016145612 A1 | 9/2016 |
| WO | WO2016145613 A1 | 9/2016 |
| WO | WO2016145656 A1 | 9/2016 |
| WO | WO2016149942 A1 | 9/2016 |
| WO | WO2016150019 A1 | 9/2016 |
| WO | WO2016154792 A1 | 10/2016 |
| WO | WO2016154797 A1 | 10/2016 |
| WO | WO2016154798 A1 | 10/2016 |
| WO | WO2016154895 A1 | 10/2016 |
| WO | WO2016154897 A1 | 10/2016 |
| WO | WO2016154994 A1 | 10/2016 |
| WO | WO2016155103 A1 | 10/2016 |
| WO | WO2016155316 A1 | 10/2016 |
| WO | WO2016161554 A1 | 10/2016 |
| WO | WO2016165055 A1 | 10/2016 |
| WO | WO2016165057 A1 | 10/2016 |
| WO | WO2016171997 A3 | 10/2016 |
| WO | WO2016172898 A1 | 11/2016 |
| WO | WO2016172908 A1 | 11/2016 |
| WO | WO2016172909 A1 | 11/2016 |
| WO | WO2016172954 A1 | 11/2016 |
| WO | WO2016174179 A1 | 11/2016 |
| WO | WO2016177604 A1 | 11/2016 |
| WO | WO2016179776 A1 | 11/2016 |
| WO | WO2016184247 A1 | 11/2016 |
| WO | WO2016187803 A1 | 12/2016 |
| WO | WO2016187943 A1 | 12/2016 |
| WO | WO2016193336 A1 | 12/2016 |
| WO | WO2016193705 A3 | 12/2016 |
| WO | WO2016200259 A1 | 12/2016 |
| WO | WO2016202033 A1 | 12/2016 |
| WO | WO2016202304 A1 | 12/2016 |
| WO | WO2016207357 A1 | 12/2016 |
| WO | WO2016208760 A1 | 12/2016 |
| WO | WO2017005835 A1 | 1/2017 |
| WO | WO2017015791 A1 | 2/2017 |
| WO | WO2017015794 A1 | 2/2017 |
| WO | WO2017015832 A1 | 2/2017 |
| WO | WO2017020275 A1 | 2/2017 |
| WO | WO2017021536 A3 | 2/2017 |
| WO | WO2017024478 A1 | 2/2017 |
| WO | WO2017024926 A1 | 2/2017 |
| WO | WO2017028167 A1 | 2/2017 |
| WO | WO2017035720 A1 | 3/2017 |
| WO | WO2017036818 A1 | 3/2017 |
| WO | WO2017036819 A1 | 3/2017 |
| WO | WO2017036865 A1 | 3/2017 |
| WO | WO2017036879 A1 | 3/2017 |
| WO | WO2017045132 A1 | 3/2017 |
| WO | WO2017045897 A1 | 3/2017 |
| WO | WO2017045898 A1 | 3/2017 |
| WO | WO2017045899 A1 | 3/2017 |
| WO | WO2017049653 A1 | 3/2017 |
| WO | WO2017049654 A1 | 3/2017 |
| WO | WO2017051348 A1 | 3/2017 |
| WO | WO2017051349 A1 | 3/2017 |
| WO | WO2017051350 A2 | 3/2017 |
| WO | WO2017054424 A1 | 4/2017 |
| WO | WO2017055564 A1 | 4/2017 |
| WO | WO2017055866 A1 | 4/2017 |
| WO | WO2017060279 A1 | 4/2017 |
| WO | WO2017063535 A1 | 4/2017 |
| WO | WO2017064051 A1 | 4/2017 |
| WO | WO2017064323 A1 | 4/2017 |
| WO | WO2017064324 A1 | 4/2017 |
| WO | WO2017066938 A1 | 4/2017 |
| WO | WO2017070871 A1 | 5/2017 |
| WO | WO2017071297 A1 | 5/2017 |
| WO | WO2017072239 A1 | 5/2017 |
| WO | WO2017072277 A1 | 5/2017 |
| WO | WO2017072284 A1 | 5/2017 |
| WO | WO2017075975 A1 | 5/2017 |
| WO | WO2017081176 A3 | 5/2017 |
| WO | WO2017082728 A1 | 5/2017 |
| WO | WO2017084488 A1 | 5/2017 |
| WO | WO2017084489 A1 | 5/2017 |
| WO | WO2017088660 A1 | 6/2017 |
| WO | WO2017092144 A1 | 6/2017 |
| WO | WO2017093452 A1 | 6/2017 |
| WO | WO2017097821 A1 | 6/2017 |
| WO | WO2017101058 A1 | 6/2017 |
| WO | WO2017102633 A1 | 6/2017 |
| WO | WO2017107546 A1 | 6/2017 |
| WO | WO2017108394 A1 | 6/2017 |
| WO | WO2017108429 A1 | 6/2017 |
| WO | WO2017113106 A1 | 7/2017 |
| WO | WO2017114389 A1 | 7/2017 |
| WO | WO2017117725 A1 | 7/2017 |
| WO | WO2017117742 A1 | 7/2017 |
| WO | WO2017118135 A1 | 7/2017 |
| WO | WO2017121253 A1 | 7/2017 |
| WO | WO2017121296 A1 | 7/2017 |
| WO | WO2017121546 A1 | 7/2017 |
| WO | WO2017122196 A1 | 7/2017 |
| WO | WO2017124957 A1 | 7/2017 |
| WO | WO2017137554 A1 | 8/2017 |
| WO | WO2017139963 A1 | 8/2017 |
| WO | WO2017143494 A1 | 8/2017 |
| WO | WO2017143495 A1 | 8/2017 |
| WO | WO2017143953 A1 | 8/2017 |
| WO | WO2017149288 A1 | 9/2017 |
| WO | WO2017153270 A1 | 9/2017 |
| WO | WO2017156694 A1 | 9/2017 |
| WO | WO2017163045 A1 | 9/2017 |

(56) References Cited

FOREIGN PATENT DOCUMENTS

| WO | WO2017163046 A1 | 9/2017 |
| WO | WO2017163050 A1 | 9/2017 |
| WO | WO2017163051 A1 | 9/2017 |
| WO | WO2017163052 A1 | 9/2017 |
| WO | WO2017164474 A1 | 9/2017 |
| WO | WO2017166334 A1 | 10/2017 |
| WO | WO2017167169 A1 | 10/2017 |
| WO | WO2017167513 A1 | 10/2017 |
| WO | WO2017173951 A1 | 10/2017 |
| WO | WO2017177897 A1 | 10/2017 |

* cited by examiner

VAPORIZER CARTRIDGE

CROSS REFERENCE TO RELATED APPLICATIONS

This application claims the benefit of U.S. Provisional Application Ser. No. 62/433,012, filed Dec. 12, 2016 and U.S. Provisional Application Ser. No. 62/511,047, filed May 25, 2017, the disclosures of each of which are hereby incorporated herein by reference in their entireties.

BACKGROUND

1. Technical Field

This disclosure relates generally to vaporizers, and more particularly to a cartridge for a vaporizer.

2. Background Information

Vaporizers have recently emerged as a new product for providing nicotine and other products through a smokeless inhalation process. There are many embodiments of vaporizers including the electronic cigarette. Most implementations consist of a power supply (typically a battery) and an atomizing device. In reusable electronic cigarettes the two items are separated into a battery and a cartomizer, to allow the disposal and replacement of the nicotine containing fluid cartomizer while preserving the more costly battery and associated circuitry (microcontroller, switch, indicating LED, etc.) In disposable electronic cigarettes the two items are combined to integrate the functions into one unit that is disposed of after either the battery energy or the nicotine containing E-liquid is exhausted.

The E-liquid that is used to produce vapor in electronic cigarettes is generally a solution of one or more of propylene glycol (PG) and/or vegetable glycerin (VG) and/or polyethylene glycol 400 (PEG400) mixed with concentrated flavors, and optionally, a variable percentage of a liquid nicotine concentrate. This liquid may be termed an "E-liquid" and is often sold in a bottle or in disposable cartridges or cartomizers. Many different flavors of such E-liquids are sold, including flavors that resemble the taste of regular tobacco, menthol, vanilla, coffee, cola and various fruits. Various nicotine concentrations are also available, and nicotine-free E-Liquids are common.

BRIEF SUMMARY

In one aspect, a refillable cartridge for a vaporizer is disclosed. The refillable cartridge may include a body housing a reservoir for storing a vaporizing product. The refillable cartridge may further include a lower ceramic pad with a through hole providing access to the reservoir. The refillable cartridge may further include a lid slidably fastened to the upper end of the body. The refillable cartridge may further include an upper ceramic pad positioned at a lower end of the lid. The upper ceramic pad may seal the through hole when the lid is slid to a first position and uncover the through hole when the lid is slid to a second position.

DETAILED DESCRIPTION

The following detailed description and the appended drawings describe and illustrate some embodiments of the disclosure for the purpose of enabling one of ordinary skill in the relevant art to make and use these embodiments. As such, the detailed description and illustration of these embodiments are purely illustrative in nature and are in no way intended to limit the scope of the disclosure in any manner. It should also be understood that the drawings are not necessarily to scale and in certain instances details may have been omitted, which are not necessary for an understanding of the embodiments, such as details of fabrication and assembly. In the accompanying drawings, like numerals represent like components.

Figure 1:
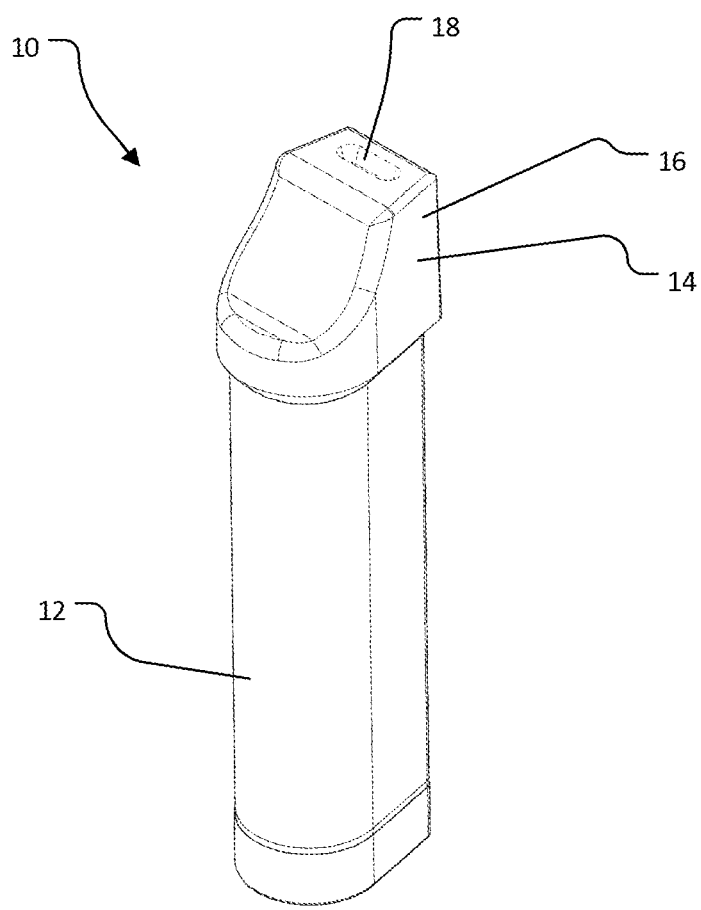
FIG. 1 illustrates a perspective view of a cartridge for a vaporizer.

FIG. 1 illustrates a perspective view of a cartridge 10 for a vaporizer. Cartridge 10 includes a body 12 and a lid 14. Lid 14 includes a mouthpiece 16 having a passageway 18 for the passage of inhalable vapor. A vaporizable material, such as E-Liquid, can be or is stored within body 12. The outer surface of body 12 is sized and shaped complementary to a vaporizer. For example, the vaporizer may have a cavity sized and shaped to receive body 12. In some embodiments, cartridge 10 may have an atomizer assembly including an atomizer within the body 12. When electrical power is supplied to the atomizer, it heats E-Liquid turning it into vapor. In other embodiments, the atomizer may be separate from cartridge 10, such that cartridge 10 delivers the E-liquid to a separate atomizer, which then heats the E-Liquid for vaporization. Once vaporized, the E-Liquid vapor mixes with air supplied from an air source (for example, from external environment) and the air-vapor mixture passes out passageway 18 in mouthpiece 16.

Figure 2:
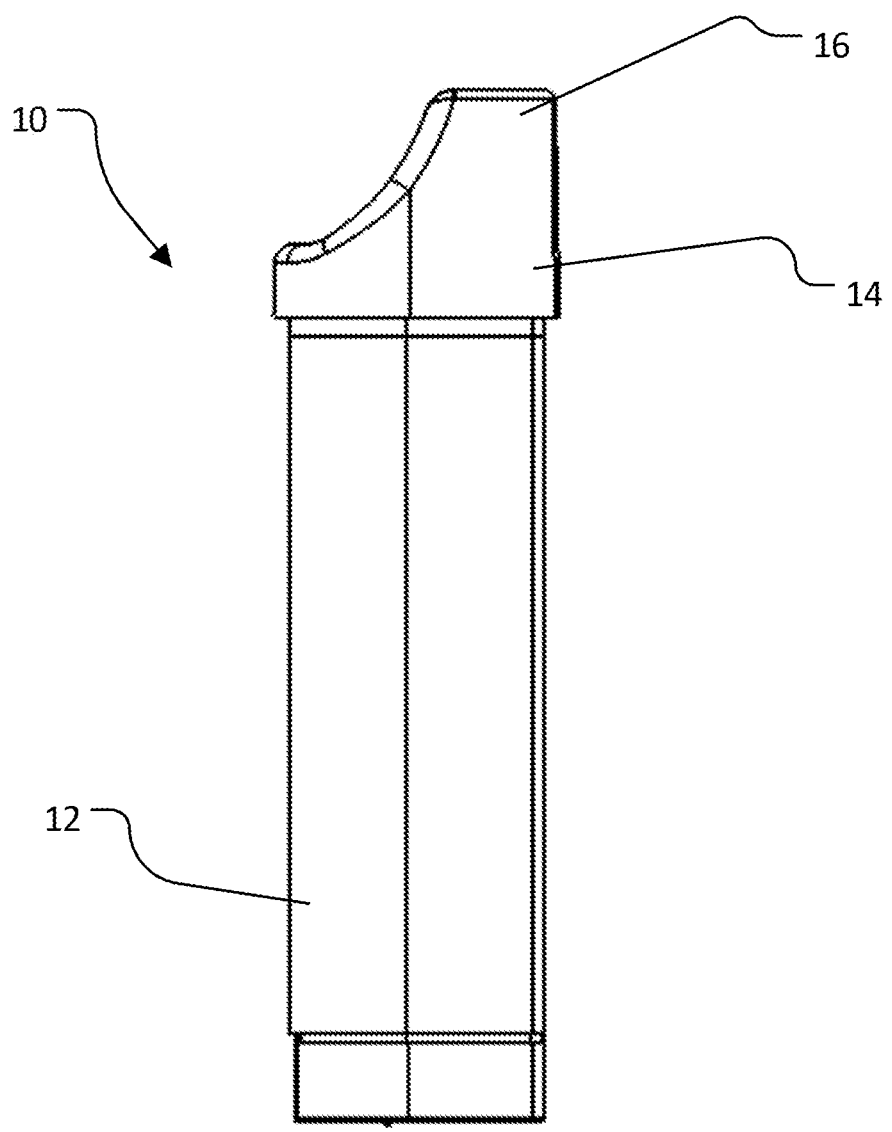
FIG. 2 illustrates a side view of the cartridge of FIG. 1 with a lid closed.
Figure 3:
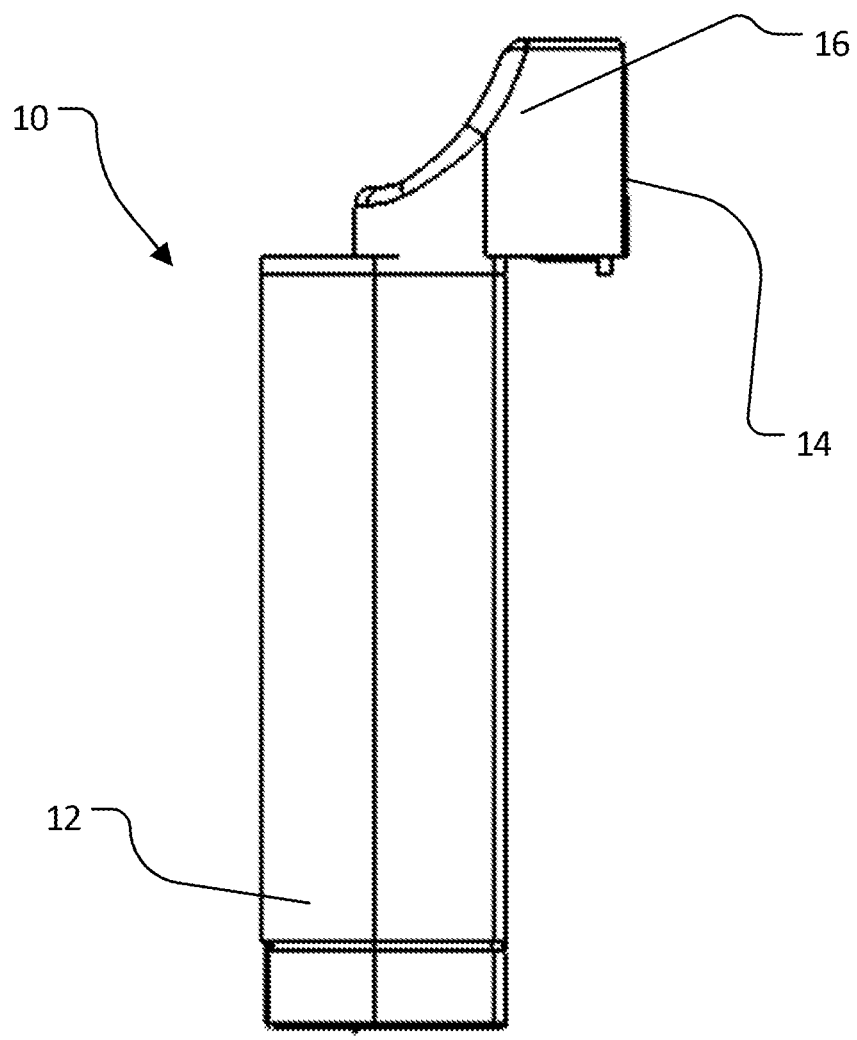
FIG. 3 illustrates a side view of the cartridge of FIG. 1 with the lid opened.

FIG. 2 illustrates a side view of cartridge 10 for a vaporizer and FIG. 3 illustrates a side view of cartridge 10 with lid 14 being opened. Lid 14 is secured to body 12 in a sliding arrangement such that lid 14 may be moved between the position shown in FIG. 2 and the position shown in FIG. 3. Lid 14 is secured to body 12 using techniques known to those of skill in the art, such as interfacing grooves and rails. Lid 14 may lock at each of the positions shown in FIG. 2 and FIG. 3. With lid 14 in the position shown in FIG. 3, an inlet to a reservoir within body 12 is exposed, allowing the reservoir to be filled with vaporizable material. In some embodiments, cartridge 10 may have an interlock so that it may only be filled when it is not coupled with the vaporizer, in other embodiments it may only be filled when cartridge 10 is coupled with the vaporizer, and in still other embodiments, the cartridge may be filled when either coupled or not coupled to the vaporizer.

Figure 4:
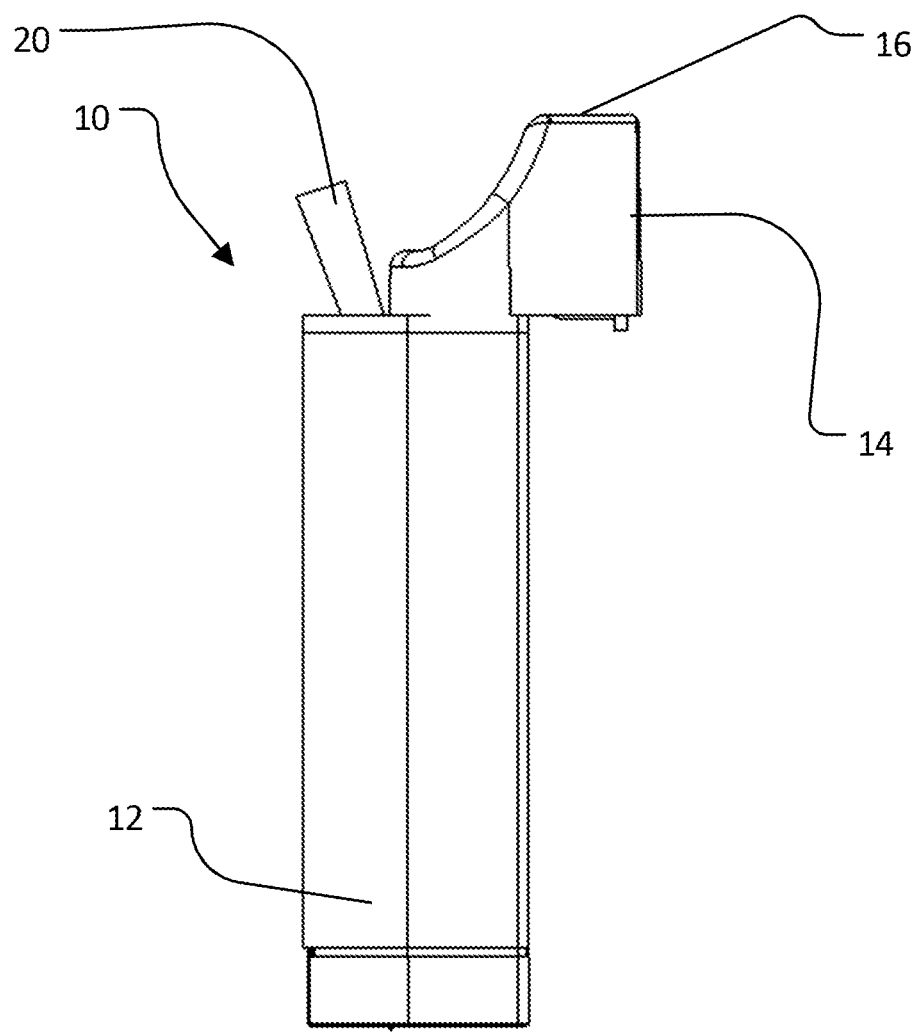
FIG. 4 illustrates a side view of the cartridge of FIG. 1 with the lid opened and a nozzle inserted to fill the cartridge with vaporizable material.

FIG. 4 illustrates a side view of cartridge 10 with a nozzle 20 being inserted into inlet 22 that is exposed when lid 14 is slid open. In certain embodiments, the lid slides in a plane substantially perpendicular to a longitudinal axis of the cartridge. With nozzle 20 inserted into the inlet 22 (see FIG. 6), the reservoir may be filled with vaporizable material.

Figure 5:
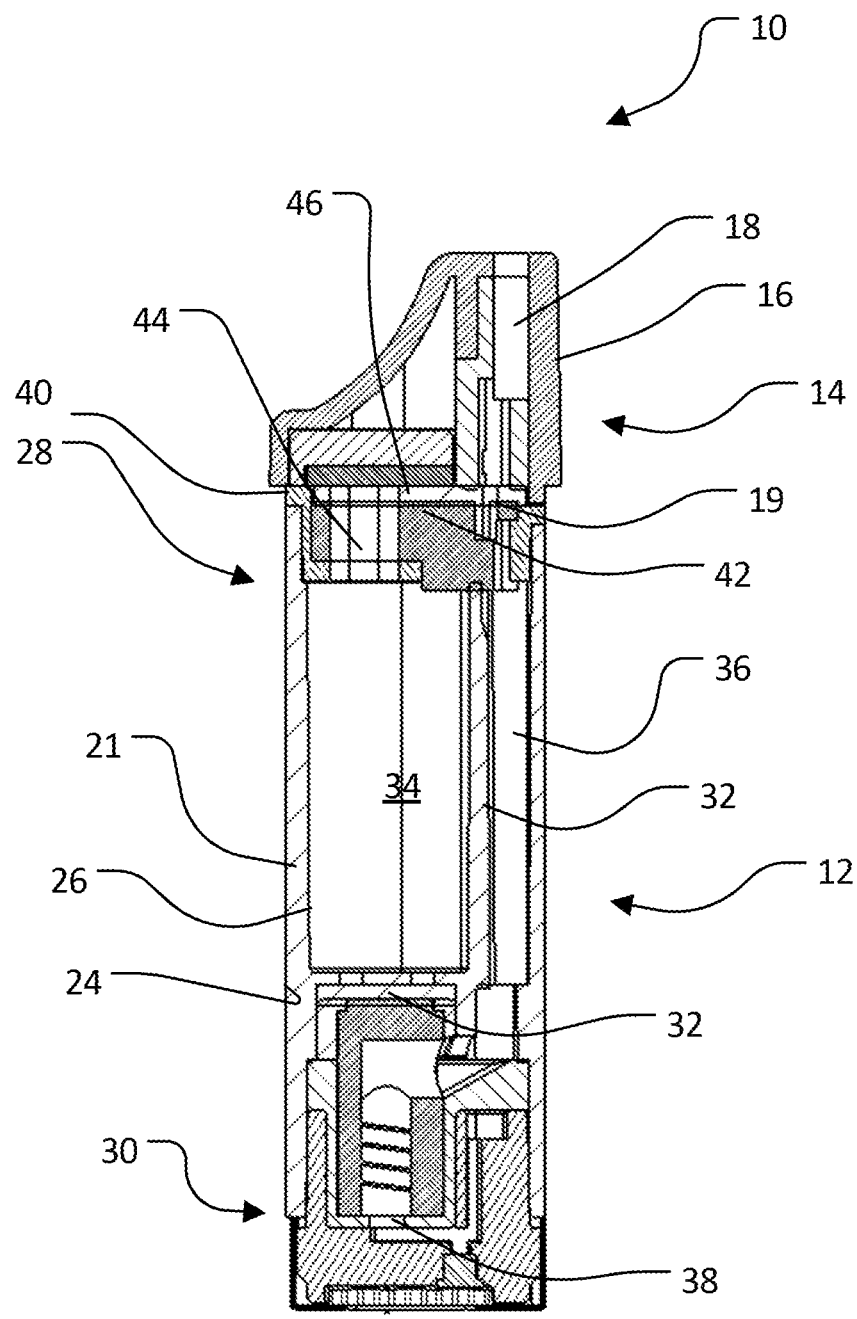
FIG. 5 illustrates a cross sectional view of the cartridge of FIG. 1 with the lid closed, showing internal construction.

FIG. 5 illustrates a cross sectional view of cartridge 10 showing an internal construction of an exemplary embodiment. In the embodiment of FIG. 5, body 12 is generally a hollow cylindrical shape. Other shapes are possible such as a hollow elongated cuboid or a hollow elliptical cylinder. A wall 21 defines an outer surface 24 of body 12 and an inner cavity 26. Inner cavity 26 is open at a top end 28 and a bottom end 30 to allow for receiving of components. The inner cavity 26 may be partitioned into separate spaces by one or more webs 32. In the embodiment of FIG. 5, inner cavity 26 is partitioned into a reservoir 34 and an air channel 36.

An atomizer assembly 38 is disposed in bottom end 30 of cavity 26 and may be held in place through a press fit, adhesive, threaded connection, or other fastening means. For example, atomizer assembly 38 may have an external thread that is complementary to an internal thread at the bottom end 30 of cavity 26. Atomizer assembly 38 may be a standard atomizer as known by one of ordinary skill in the art. Atomizer assembly 38 receives product from reservoir 34 and heats the vaporizable material until it vaporizes. The vapor is mixed with a flow of air and passes to mouthpiece 16 through air channel 36.

At top end 28, a cap 40 is secured within cavity 26. Cap 40 is attached to body 12 through conventional means such as a press fit, adhesive, threads, etc. Cap 40 includes a lower ceramic pad 42 disposed at an outer surface of the cap 40. Lower ceramic pad 42 has a through-hole 44 passing from an external surface of the pad to the reservoir 34. In the configuration shown in FIG. 5, lower ceramic pad 42 is covered by lid 14, sealing the through-hole so that no product may escape through lower ceramic pad.

Lid 14 has a corresponding upper ceramic pad 46 for sealing the through-hole of the lower ceramic pad 42. In the configuration of FIG. 5, upper ceramic pad 46 contacts lower ceramic pad 42, sealing the through-hole to prevent leakage of the product. Additionally, in the configuration of FIG. 5, an outlet 19 of mouthpiece 16 aligns with passageway 36, allowing air to flow from the passageway to the mouthpiece 16.

Figure 6:
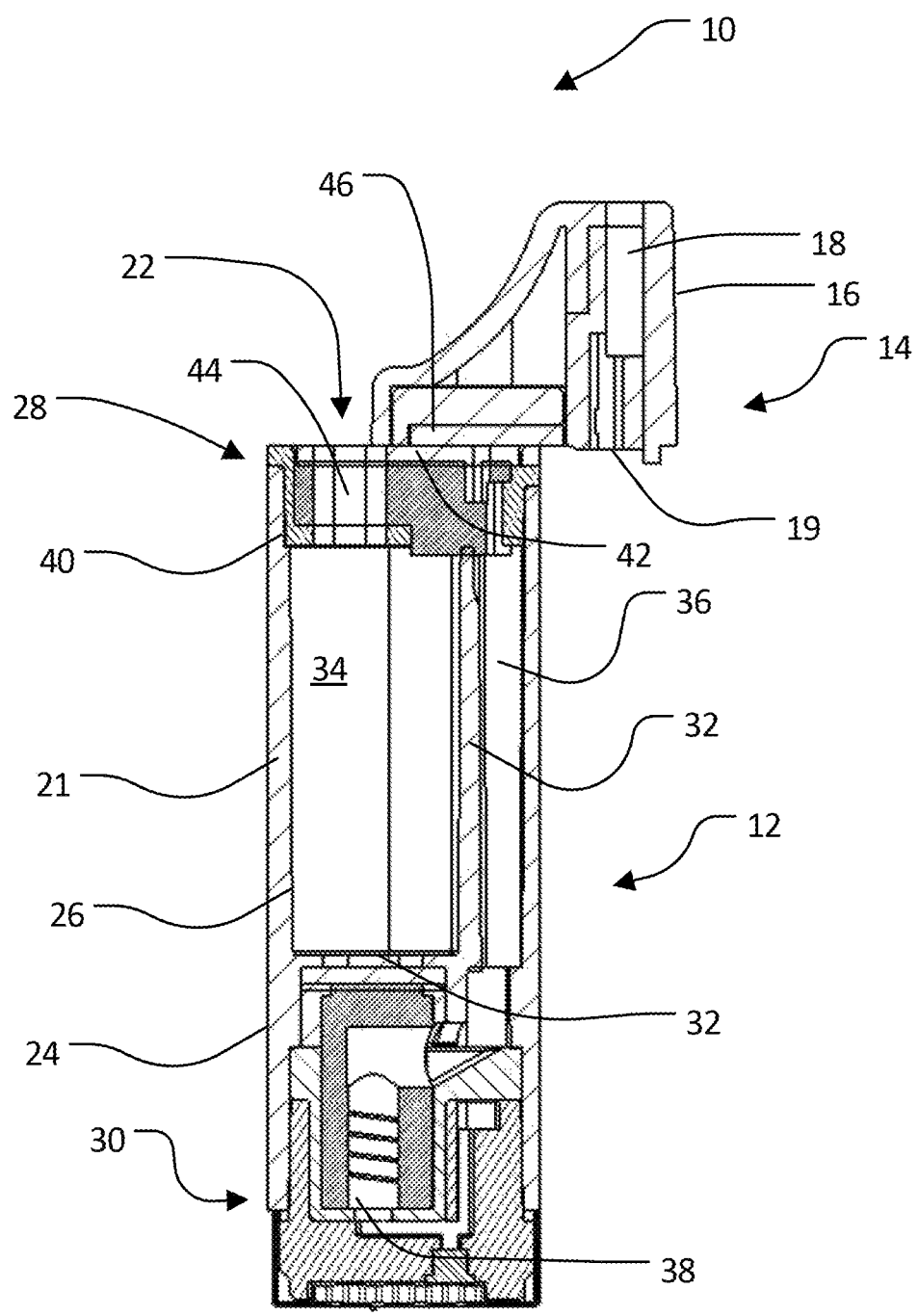
FIG. 6 illustrates a cross sectional view of the cartridge of FIG. 1 with the lid opened, showing internal construction.

FIG. 6 illustrates the embodiment of FIG. 5 with lid 14 being slid to a second configuration. In this second configuration, upper ceramic pad 46 has been moved laterally such that it is no longer covering through-hole 44, allowing access to reservoir 34 through through-hole 44. In some embodiments, upper ceramic pad 46 may cover passageway 36 when in the second configuration.

Figure 7:
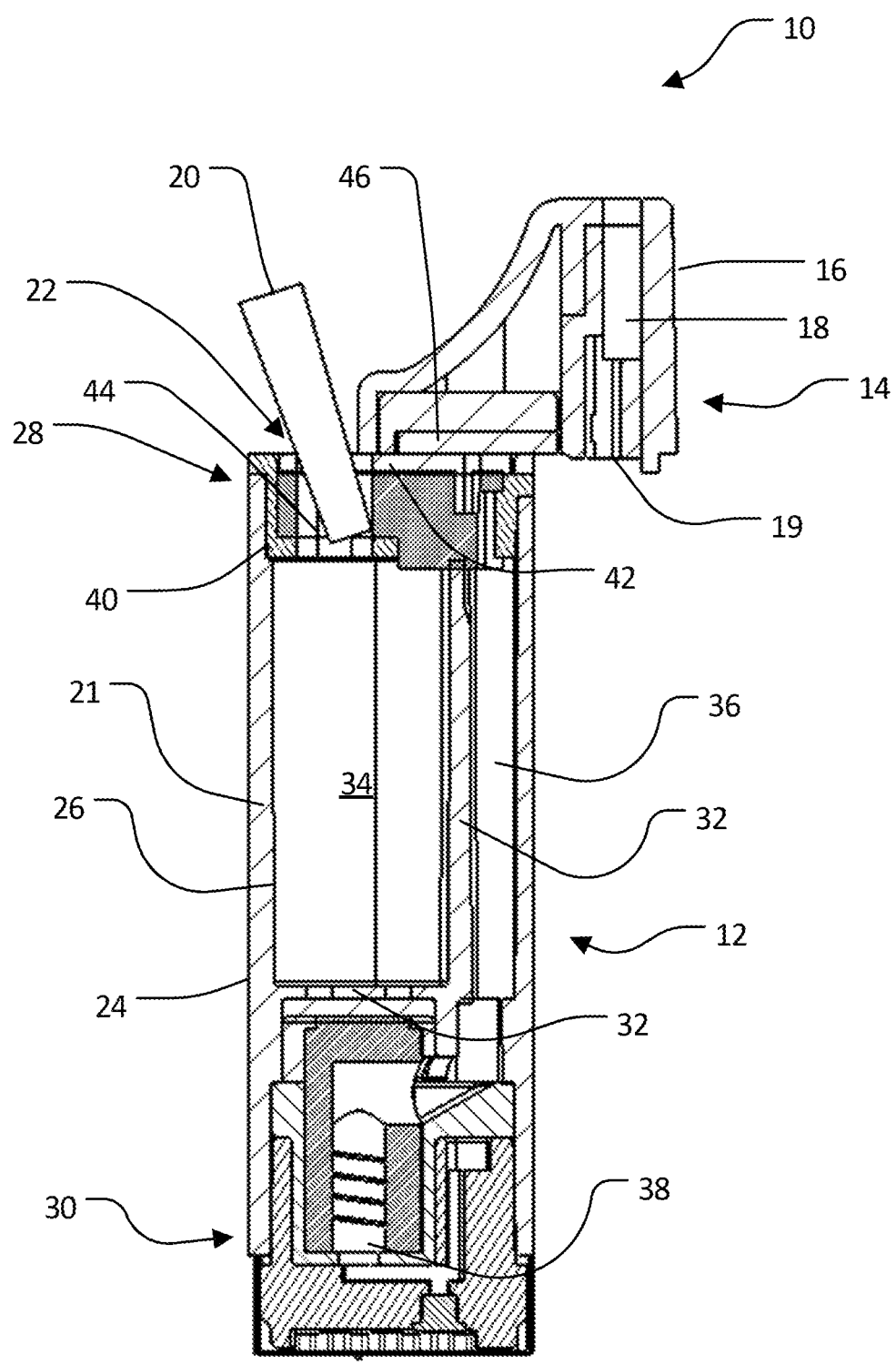
FIG. 7 illustrates a cross sectional view of the cartridge of FIG. 1 with the lid opened and the nozzle inserted to fill the cartridge with vaporizable material, showing internal construction.

FIG. 7 illustrates the embodiment of FIG. 5 in the second configuration, but with nozzle 20 being inserted into through-hole 44. Vaporizable material, such as E-liquid, may be delivered by nozzle 20 into reservoir 34. After a desired quantity of product is delivered to the reservoir, nozzle 20 is removed from the through-hole and lid 14 is slid laterally, back to the configuration of FIG. 5. The upper ceramic pad 46 and the lower ceramic pad 42 are placed against one another, inhibiting the product from flowing out of the reservoir through the through-hole. The ceramic pads are durable to abrasion allowing them to be slid back and forth without losing their ability to seal. Because vaporizable material is typically more viscous than water or many other fluids, it does not leak past the interface of the ceramic pads.

Some embodiments of the present disclosure include methods of filling or refilling a refillable cartridge of the present disclosure as described hereinthroughout. For example, certain methods comprise providing a refillable cartridge according to the present disclosure, laterally sliding the lid from the lid's first position to the second position; and providing through the through hole the vaporizable material to the reservoir. In other embodiments, the methods further comprise laterally sliding the lid from the second position to the first position after providing the vaporizable material to the reservoir.

Certain other embodiments of the present disclosure are directed to kits comprising the refillable cartridge according to the present disclosure along with instructions for filling or refilling the reservoir. In some embodiments, the kits further comprise a nozzle for supplying vaporizable material to the reservoir. In some other embodiments, the kits further comprise a vaporizable material, typically within a container for holding the particular vaporizable material. In yet other embodiments, the kits comprise the refillable cartridge according to the present disclosure, instructions for filling or refilling the reservoir, a nozzle for supplying vaporizable material to the reservoir and a vaporizable material, typically within a container for holding the particular vaporizable material. In some embodiments, the upper ceramic pad 46 and the lower ceramic pad 42 are biased towards one another. This bias may be provided by tracks configured to guide lid 14 as it slides across to the top of the body to close. In some embodiments, the cartridge may have an interlock so that it may only be filled when it is not in the vaporizer, or that it may only be filled when it is in the vaporizer.

The descriptions set forth above are meant to be illustrative and not limiting. Various modifications of the disclosure, in addition to those described herein, will be apparent to those skilled in the art from the foregoing description. Such modifications are also intended to fall within the scope of the concepts described herein. The disclosures of each patent, patent application and publication cited or described in this document are hereby incorporated herein by reference, in their entireties.

The foregoing description of possible implementations consistent with the present disclosure does not represent a comprehensive list of all such implementations or all variations of the implementations described. The description of some implementation should not be construed as an intent to exclude other implementations. For example, artisans will understand how to implement the disclosure in many other ways, using equivalents and alternatives that do not depart from the scope of the disclosure. Moreover, unless indicated to the contrary in the preceding description, none of the components described in the implementations are essential to the disclosure. It is thus intended that the embodiments disclosed in the specification be considered as illustrative, with a true scope and spirit of the disclosure being indicated by the following claims.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

The invention claimed is:

1. A refillable cartridge for a vaporizer, comprising:
   a body having a wall defining a cavity, the body housing a reservoir for storing vaporizable material;

a cap including a lower ceramic pad positioned proximate an upper end of the body, the lower ceramic pad having a through-hole providing an access to the reservoir;

a lid adjacent to the cap and slidably fastened to the upper end of the body, the lid configured to slide in a linear direction that is substantially perpendicular to a longitudinal axis of the cartridge; and an upper ceramic pad positioned at a lower end of the lid, the upper ceramic pad sealing the through-hole when the lid is located at a first position and uncovering the through hole when the lid is slid to a second position.

2. The refillable cartridge according to claim 1, wherein the lid includes a mouthpiece having a passageway for providing an inhalable vapor to a vaporizer user from an atomizer within a vaporizer.

3. The refillable cartridge according to claim 1, further comprising an atomizer for converting the vaporizable material into a vapor for inhalation.

4. The refillable cartridge according to claim 1, wherein the cartridge does not contain an atomizer within the body for converting the vaporizable material into a vapor for inhalation.

5. The refillable cartridge according to claim 1, wherein, when the lid is in the first position, the upper and lower ceramic pads are biased toward one another to thereby create a seal between the upper and lower ceramic pads.

6. The refillable cartridge according to claim 1, wherein, when the lid is slid to the second position the through-hole is exposed to thereby provide the access to the reservoir for filling or refilling the reservoir with the vaporizable material.

7. The refillable cartridge according to claim 1, wherein the lower ceramic pad is disposed at an outer surface of the cap.

8. A method of refilling a refillable cartridge comprising:
providing a refillable cartridge according to claim 1;
sliding the lid in the linear direction to cause the lid to slide from the first position to the second position; and
providing through the through-hole the vaporizable material to the reservoir.

9. The method according to claim 8, further comprising sliding the lid from the second position back to the first position after providing the vaporizable material to the reservoir.

10. The refillable cartridge according to claim 1 further comprising a vaporizable material in the reservoir.

11. A kit comprising the refillable cartridge according to claim 1 and instructions for filling or refilling the reservoir.

12. The kit according to claim 11, further comprising a nozzle for supplying vaporizable material to the reservoir.

13. The kit according to claim 11, further comprising a vaporizable material.

14. The method according to claim 8, wherein the lower ceramic pad is disposed at an outer surface of the cap.

* * * * *